United States Patent [19]
Jalett et al.

[11] Patent Number: 5,859,300
[45] Date of Patent: Jan. 12, 1999

[54] PROCESS FOR THE HYDROGENATION OF IMINES

[75] Inventors: Hans-Peter Jalett, Dornach, Switzerland; Bernd Siebenhaar, Kandern, Germany

[73] Assignee: Novartis Corporation, Summit, N.J.

[21] Appl. No.: 108

[22] PCT Filed: Jul. 17, 1996

[86] PCT No.: PCT/EP96/03143

§ 371 Date: Jan. 26, 1998

§ 102(e) Date: Jan. 26, 1998

[87] PCT Pub. No.: WO97/05095

PCT Pub. Date: Feb. 13, 1997

[30] Foreign Application Priority Data

Jul. 26, 1995 [CH] Switzerland .............................. 2194/95

[51] Int. Cl.$^6$ .................................................. C07C 209/52
[52] U.S. Cl. .............................. 564/143; 549/68; 564/415
[58] Field of Search ...................................... 564/143, 315, 564/415; 549/68

[56] References Cited

U.S. PATENT DOCUMENTS

| | | |
|---|---|---|
| 4,994,616 | 2/1991 | Spindler et al. . |
| 5,011,995 | 4/1991 | Pugin et al. . |
| 5,112,999 | 5/1992 | Osborn et al. . |
| 5,371,256 | 12/1994 | Togni et al. . |
| 5,430,188 | 7/1995 | Badar et al. . |
| 5,565,594 | 10/1996 | Spindler et al. . |
| 5,686,616 | 11/1997 | Tani et al. ............................... 546/185 |

FOREIGN PATENT DOCUMENTS

| | | |
|---|---|---|
| 605363 | 7/1994 | European Pat. Off. . |
| 612758 | 8/1994 | European Pat. Off. . |

*Primary Examiner*—Brian M. Burn
*Attorney, Agent, or Firm*—William A. Teoli, Jr.

[57] ABSTRACT

A process for the hydrogenation of imines with hydrogen under elevated pressure in the presence of iridium catalysts containing diphosphine ligands, with or without an inert solvent, the reaction mixture containing a soluble ammonium chloride, bromide or iodide or a soluble metal chloride, bromide, or iodide, wherein the reaction mixture additionally contains at least one solid acid with the exception of ion exchangers. Improved optical yields and high chemical conversion rates are achieved while the catalyst is easily separable.

57 Claims, No Drawings

PROCESS FOR THE HYDROGENATION OF IMINES

This application is a 35 USC 371 of PCT/EP96/03143, filed Jul. 13, 1996.

The present invention relates to a process for the hydrogenation of imines with hydrogen and with iridium-diphosphine complexes under elevated pressure in the presence of solid acids.

U.S. Pat. No. 4,994,615 describes a process for the asymmetric hydrogenation of prochiral N-arylketimines wherein iridium catalysts having chiral diphosphine ligands are used. U.S. Pat. No. 5,011,995 describes a process for the asymmetric hydrogenation of prochiral N-alkylketimines using the same catalysts. U.S. Pat. No. 5,112,999 discloses polynuclear iridium compounds and a complex salt of iridium, which contain diphosphine ligands, as catalysts for the hydrogenation of imines. U.S. Pat. No. 5,371,256 and EP-A-0 612 758 describe iridium complexes with chiral ferrocenyldiphosphine ligands for the homogeneous enantioselective hydrogenation of imines.

Those homogeneous catalysis processes have proved valuable, although it is evident, especially in the case of relatively large batches or on an industrial scale, that the catalysts frequently tend to become deactivated to a greater or lesser extent depending on the catalyst precursor, the substrate and the diphosphine ligands that are used. In many cases, especially at elevated temperatures—for example at temperatures >25° C., which are necessary for a short reaction time—it is not possible to achieve complete conversion. For industrial applications of the hydrogenation processes, therefore, the catalyst productivity is too low to be economically viable. Those disadvantages are also not eliminated by the addition of metal halides described in U.S. Pat. No. 4,994,615, U.S. Pat. No. 5,011,995 and U.S. Pat. No. 5,112,999.

It has now been found, surprisingly, that the catalyst activity can be considerably increased if the reaction mixture contains solid acids. It has also unexpectedly been found that at the same time the deactivation of the catalysts can be considerably reduced or completely eliminated. It has also been found, surprisingly, that when asymmetric catalysts are used the enantioselectivity is high, and high optical yields of up to 80% can be achieved, even at reaction temperatures of more than 50° C. In addition, it is of particular advantage to the working-up of the reaction mixture that the solid acids can be removed from the reaction mixture simply by filtration. It has also unexpectedly been found that it is even possible to obtain higher conversion rates and optical yields using a smaller amount of catalyst, which offers very considerable economic advantages since the molar ratio of imine to iridium catalyst can be greatly increased.

The invention relates to a process for the hydrogenation of imines with hydrogen under elevated pressure in the presence of iridium catalysts containing diphosphine ligands, with or without an inert solvent, the reaction mixture containing a soluble ammonium chloride, bromide or iodide or a metal chloride, bromide or iodide, wherein the reaction mixture additionally contains at least one solid acid with the exception of ion exchangers.

Suitable imines are especially those which contain at least one >C=N— group. If the groups are substituted asymmetrically and are thus compounds having a prochiral ketimine group, it is possible in the process according to the invention for mixtures of optical isomers or pure optical isomers to be formed if enantioselective or diastereoselective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group >C=N— may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl wherein halogen is preferably F or Cl, —CN, —$NO_2$, —$CO_2H$, —$CONH_2$, —$SO_3H$, —$PO_3H_2$, or by $C_1$–$C_{12}$alkyl esters, $C_1$–$C_{12}$alkylamides, phenyl esters or benzyl esters of the groups —$CO_2H$, —$SO_3H$ and —$PO_3H_2$. Aldimine and ketimine groups are especially reactive, with the result that using the process according to the invention it is possible selectively to hydrogenate >C=N— groups in addition to the >C=C< and/or >C=O groups. Aldimine and ketimine groups are also to be understood to include >C=N—N— hydrazone groups.

The process according to the invention is suitable especially for the hydrogenation of aldimines, ketimines and hydrazones with the formation of corresponding amines and hydrazines, respectively. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, preferably higher than 50%, and yields of more than 90% being achievable. The optical yield indicates the ratio of the two stereoisomers formed, which ratio may be, for example, greater than 2:1 and is preferably greater than 4:1.

The imines are preferably imines of formula I

which are hydrogenated to form amines of formula II

wherein $R_3$ is preferably a substituent and wherein $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom or $C_1$–$C_{12}$alkyl substituted by the mentioned cycloalkyl or heterocycloalkyl or heteroaryl; or wherein $R_3$ is $C_6$–$C_{12}$aryl, or $C_4$–$C_{11}$ heteroaryl bonded via a ring carbon atom and having 1 or 2 hetero atoms in the ring; $R_3$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —CONR$_4$R$_5$ or by —COOR$_4$; $C_6$–$C_{12}$aryl or $C_7$–$C_{16}$aralkyl that is unsubstituted or substituted as $R_3$, or —CONR$_4$R$_5$ or —COOR$_4$, wherein $R_4$ and $R_5$ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —NR$_6$— radicals, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defmed hereinbefore and $R_1$ and $R_3$ together are alkylene having from 2 to 5 carbon atoms that is optionally interrupted by 1 or 2 —O—, —S— or —NR$_6$— radicals, and/or unsubstituted or substituted by =O or as $R_1$ and $R_2$ above in the meaning of alkyl, and/or condensed with benzene, pyridine, pyrimidine, furan, thiophene or pyrrole.

The radicals $R_1$, $R_2$ and $R_3$ may contain one or more centres of chirality.

$R_1$, $R_2$ and $R_3$ may be substituted in any desired positions by identical or different radicals, for example by from 1 to 5, preferably from 1 to 3, substituents.

Suitable substituents for $R_1$ and $R_2$ and $R_3$ are: $C_1$–$C_{12}$-, preferably $C_1$–$C_6$-, and especially $C_1$–$C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals;

$C_1$–$C_6$haloalkyl, preferably $C_1$–$C_4$haloalkyl, having preferably F and Cl as halogen, e.g. tri-fluoro- or trichloro-methyl, difluorochloromethyl, fluorodichloromethyl, 1,1-difluoro-eth-1-yl, 1,1-dichloroeth-1-yl, 1,1,1-trichloro- or 1,1,1-trifluoro-eth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-eth-2-yl or -eth-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but-4yl, 2,3-dichloro-prop-1-yl, 1-chloro-2-fluoro-prop-3-yl, 2,3-dichlorobut-1-yl;

$C_6$–$C_{12}$-aryl, -aryloxy or -arylthio, in which aryl is preferably naphthyl and especially phenyl, $C_7$–$C_{16}$-aralkyl, -aralkoxy and -aralkylthio, in which the aryl radical is preferably naphthyl and especially phenyl and the alkylene radical is linear or branched and contains from 1 to 10, preferably from 1 to 6 and especially from 1 to 3, carbon atoms, for example benzyl, naphthylmethyl, 1- or 2-phenyl-eth-1-yl or -eth-2-yl, 1-, 2- or 3-phenyl-prop-1-yl, -prop-2-yl or -prop-3-yl, with benzyl being especially preferred; the radicals containing the aryl groups mentioned above may in turn be mono- or poly-substituted, for example by $C_1$–$C_4$-alkyl, -alkoxy or -alkylthio, halogen, —OH, —CONR$_4$R$_5$ or by —COOR$_5$, wherein $R_4$ and $R_5$ are as defined; examples are methyl, ethyl, n- and iso-propyl, butyl, corresponding alkoxy and alkylthio radicals, F, Cl, Br, dimethyl-, methyl ethyl- and diethyl-carbamoyl and methoxy-, ethoxy-, phenoxy- and benzyloxy-carbonyl;

halogen, preferably F and Cl;

secondary amino having from 2 to 24, preferably from 2 to 12 and especially from 2 to 6, carbon atoms, the secondary amino preferably containing 2 alkyl groups, for example dimethyl-, methylethyl-, diethyl-, methylpropyl-, methyl-n-butyl-, di-n-propyl-, di-n-butyl-or di-n-hexyl-amino;

—CONR$_4$R$_5$, wherein $R_4$ and $R_5$ are each independently of the other $C_1$–$C_{12}$alkyl, preferably $C_1$–$C_6$alkyl, and especially $C_1$–$C_4$alkyl, or $R_4$ and $R_5$ together are tetra- or penta-methylene or 3-oxapentylene, the alkyl being linear or branched, e.g. dimethyl-, methyl-ethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl;

—COOR$_4$, wherein $R_4$ is $C_1$–$C_{12}$alkyl, preferably $C_1$–$C_6$alkyl, which may be linear or branched, e.g. methyl, ethyl, n- and iso-propyl, n-, iso- and tert-butyl, and the isomers of pentyl, hexyl, heptyl, octyl, nonyl, decyl, undecyl and dodecyl.

$R_1$, $R_2$ and $R_3$ may contain especially functional groups, such as keto groups, —CN, —NO$_2$, carbon double bonds, N—O—, aromatic halogen groups and amide groups.

$R_1$ and $R_2$ as heteroaryl are preferably a 5- or 6-membered ring having 1 or 2 identical or different hetero atoms, especially O, S or N, which contains preferably 4 or 5 carbon atoms and can be condensed with benzene. Examples of heteroaromatics from which $R_1$ can be derived are furan, pyrrole, thiophene, pyridine, pyrimidine, indole and quinoline.

$R_1$ and $R_2$ as heteroaryl-substituted alkyl are derived preferably from a 5- or 6-membered ring having 1 or 2 identical or different hetero atoms, especially O, S or N, which contains preferably 4 or 5 carbon atoms and can be condensed with benzene. Examples of hetero-aromatics are furan, pyrrole, thiophene, pyridine, pyrimidine, indole and quinoline.

$R_1$ and $R_2$ as heterocycloalkyl or as heterocycloalkyl-substituted alkyl contain preferably from 4 to 6 ring atoms and 1 or 2 identical or different hetero atoms from the group O, S and NR$_6$. It can be condensed with benzene. It may be derived, for example, from pyrrolidine, tetrahydrofuran, tetrahydrothiophene, indane, pyrazolidine, oxazolidine, piperidine, piperazine or morpholine.

$R_1$, $R_2$ and $R_3$ as alkyl are preferably unsubstituted or substituted $C_1$–$C_6$alkyl, especially $C_1$–$C_4$alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_1$, $R_2$ and $R_3$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_1$, $R_2$ and $R_3$ as aryl are preferably unsubstituted or substituted naphthyl and especially phenyl. $R_1$, $R_2$ and $R_3$ as aralkyl are preferably unsubstituted or substituted phenylalkyl having from 1 to 10, preferably from 1 to 6 and especially from 1 to 4, carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenyl-prop-3-yl, 2-phenylprop-1-yl, 2-phenylprop-2-yl and 1-phenylbut-4yl.

In $R_2$ and $R_3$ as —CONR$_4$R$_5$ and —COOR$_4$, $R_4$ and $R_5$ are preferably $C_1$–$C_6$alkyl, especially $C_1$–$C_4$alkyl, or $R_4$ and $R_5$ together are tetramethylene, pentamethylene or 3-oxapentylene. Examples of alkyl have been mentioned hereinbefore.

$R_1$ and $R_2$ together or $R_1$ and $R_3$ together as alkylene are preferably interrupted by one —O—, —S— or —$NR_6$- radical, preferably —O—. $R_1$ and $R_2$ together or $R_1$ and $R_3$ together form, with the carbon atom or with the —N=C group to which they are bonded, respectively, preferably a 5- or 6-membered ring. For the substituents the preferences mentioned hereinbefore apply. As condensed alkylene, RI and $R_2$ together or $R_1$ and $R_3$ together are preferably alkylene condensed with benzene or pyridine. Examples of alkylene are: ethylene, 1,2- or 1,3-propylene, 1,2-, 1,3- or 1,4butylene, 1,5-pentylene and 1,6-hexylene. Examples of interrupted or =O-substituted alkylene are 2-oxa-1,3-propylene, 2-oxa-1,4-butylene, 2-oxa- or 3-oxa-1,5-pentylene, 3-thia- 1,5-pentylene, 2-thia- 1,4-butylene, 2-thia- 1,3-propylene, 2-methylimino-1,3-propylene, 2-ethylimino-1,4-butylene, 2- or 3-methyl-imino-1,5-pentylene, 1-oxo-2-oxa-1,3-propylene, 1-oxo-2-oxa-1,4-butylene, 2-oxo-3-oxa-1,4-butylene, 1-oxa-2-oxo-1,5-pentylene. Examples of condensed alkylene are:

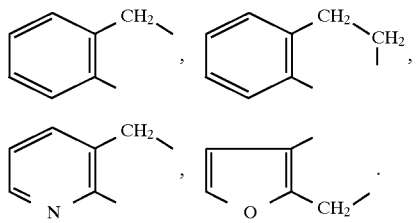

Examples of condensed and interrupted and unsubstituted or =O-substituted allylene are:

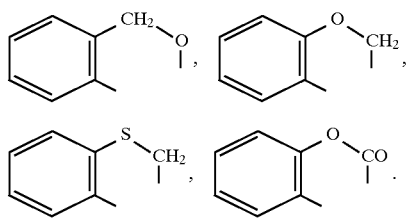

$R_4$ and $R_5$ are preferably each independently of the other hydrogen, $C_1$–$C_4$alkyl, phenyl or benzyl. $R_6$ is preferably hydrogen or $C_1$–$C_4$alkyl.

A further preferred group is formed by prochiral imines in which in formula I $R_1$, $R_2$ and $R_3$ are each different from the others and are not hydrogen.

In an especially preferred group, in formula I $R_3$ is 2,6-di-$C_1$–$C_4$alkylphen-1-yl and especially 2,6-dimethylphen-1-yl or 2-methyl-6-ethylphen-1-yl, $R_1$ is $C_1$–$C_4$alkyl and especially ethyl or methyl, and $R_2$ is $C_1$–$C_4$alkyl, $C_1$–$C_4$alkoxymethyl or $C_1$–$C_4$alkoxyethyl, and especially methoxymethyl.

Of those compounds, imines of formulae

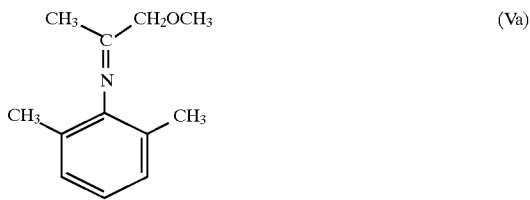

and

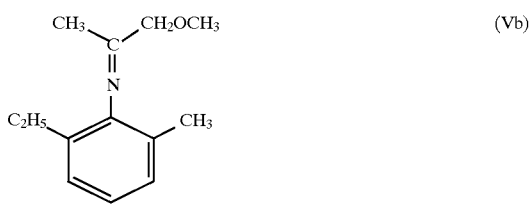

are especially important, as is the imine of formula

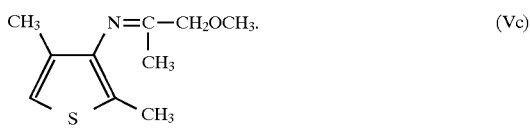

Imines of formula I are known or they can be prepared in accordance with known processes from aldehydes or ketones and primary amines.

The iridium catalysts are preferably homogeneous catalysts that are substantially soluble in the reaction medium. The term "catalyst" also includes catalyst precursors that are converted into an active catalyst species at the beginning of a hydrogenation. The catalysts preferably correspond to the formulae III, IIIa, IIIb, IIIc and IIId, $[XIrYZ]$, (III)

$[XIrY]^{\oplus}A^{\ominus}$, (IIIa)

$[YIrZ_4]^{\ominus}M^{\oplus}$, (IIIb)

$[YIrHZ_2]_2$, (IIIc)

$[YIrZ_3]_2$, (IIId)

wherein X is two olefin ligands or a diene ligand, Y is a ditertiary diphosphine
(a) the phosphine groups of which are bonded to different carbon atoms of a carbon chain having from 2 to 4 carbon atoms, or
(b) the phosphine groups of which are either bonded directly or via a bridge group —$CR_aR_b$— in the ortho positions of a cyclopentadienyl ring or are each bonded to a cyclopentadienyl ring of a ferrocenyl, or
(c) one phosphine group of which is bonded to a carbon chain having 2 or 3 carbon atoms and the other phosphine group of which is bonded to an oxygen atom or nitrogen atom bonded terminally to that carbon chain, or
(d) the phosphine groups of which are bonded to the two oxygen atoms or nitrogen atoms bonded terminally to a $C_2$-carbon chain;
with the result that in the cases of (a), (b), (c) and (d) a 5-, 6- or 7-membered ring is formed with the Ir atom, the radicals Z are each independently of the other(s) Cl, Br or I, $A^{\ominus}$ is the anion of an oxy or complex acid, and $M^{\oplus}$ is an alkali metal cation or quatemary ammonium, and $R_a$ and $R_b$ are each independently of the other hydrogen, $C_1$–$C_8$alkyl, $C_1$–$C_4$fluoroalkyl, phenyl or benzyl, or phenyl or benzyl having from 1 to 3 $C_1$–$C_4$alkyl or $C_1$–$C_4$alkoxy substituents. $R_b$ is preferably hydrogen. $R_a$ is preferably $C_1$–$C_4$alkyl and especially methyl.

The diphosphine Y contains preferably at least one chiral group and is especially an optically pure stereoisomer or a pair of diastereoisomers, since the use of catalysts containing chiral ligands leads to optical induction in asymmetric hydrogenation reactions.

X as an olefin ligand may be a branched or, preferably, linear $C_2$–$C_{12}$alkylene, especially $C_2$–$C_6$alkylene. Some examples are dodecylene, decylene, octylene, 1-, 2- or 3-hexene, 1-, 2- or 3-pentene, 1- or 2-butene, propene and ethene. X as a diene ligand may be an open-chain or cyclic diene having from 4 to 12, preferably from 5 to 8, carbon atoms, the diene groups preferably being separated by one or two saturated carbon atoms. Some examples are butadiene, pentadiene, hexadiene, heptadiene, octadiene, decadiene, dodecadiene, cyclopentadiene, cyclohexadiene, cycloheptadiene, cyclooctadiene and bridged cyclodienes such as norbornadiene and bicyclo-2,2,2-octadiene. Hexadiene, cyclooctadiene and norbornadiene are preferred.

The phosphine groups contain preferably two identical or different, preferably identical, unsubstituted or substituted hydrocarbon radicals having from 1 to 20, especially from 1 to 12, carbon atoms. Preference is given to those diphosphines wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$cycloalkyl, $C_5$–$C_{12}$cycloalkyl-$CH_2$—, phenyl or benzyl; and phenyl or benzyl substituted by halogen (e.g. F, Cl or Br), $C_1$–$C_6$haloalkyl, $(C_1$–$C_{12}$alkyl$)_3$Si, $(C_6H_5)_3$Si, $C_1$–$C_6$haloalkoxy (e.g. trifluoromethoxy), —$NH_2$, phenyl$_2$N—, benzyl$_2$N—, morpholinyl, piperidinyl, pyrrolidinyl, $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl (e.g. —$COOCH_3$), wherein $M_1$ is an alkali metal or hydrogen and $X_1^\ominus$ is the anion of a monobasic acid. $M_1$ is preferably H, Li, Na or K. $A_1^\ominus$ as the anion of a monobasic acid is preferably $Cl^\ominus$, $Br^\ominus$ or the anion of a carboxylic acid, for example formate, acetate, trichloroacetate or trifluoroacetate.

Examples of alkyl that preferably contains from 1 to 6 carbon atoms are methyl, ethyl, n-propyl, isopropyl, n-, iso- and tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-, alkoxy- or haloalkoxy-substituted phenyl and benzyl are methylphenyl, dimethylphenyl, trimethylphenyl, ethyl-phenyl, methylbenzyl, methoxyphenyl, dimethoxyphenyl, trifluoromethylphenyl, bis-tri-fluoromethylphenyl, tris-trifluoromethylphenyl, trifluoromethoxyphenyl and bis-trifluoromethoxyphenyl. Preferred phosphine groups are those which contain identical or different, preferably identical, radicals from the group $C_1$–$C_6$alkyl; cyclopentyl and cyclohexyl that are unsubstituted or have from one to three $C_1$–$C_4$alkyl or $C_1$–$C_4$alkoxy substituents, benzyl and, especially, phenyl that are unsubstituted or have from one to three $C_1$–$C_4$alkyl, $C_1$–$C_4$alkoxy, F, Cl, $C_1$–$C_4$fluoroalkyl or $C_1$–$C_4$fluoroalkoxy substituents.

A secondary phosphine group may also be a radical of the formula

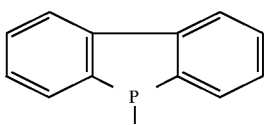

or

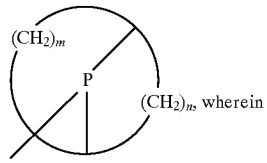 wherein m and n are each independently of the other an integer from 2 to 10, and the sum of m+n is from 4 to 12, especially from 5 to 8. Examples thereof are [3.3.1]- and [4.2.1]-phobyl of the formulae

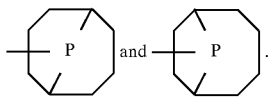

A secondary phosphine group may also be a radical of the formula

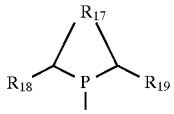

wherein $R_{17}$ is $C_1$–$C_4$alkylene, preferably $C_2$- or $C_3$-alkylene, and $R_{18}$ and $R_{19}$ are each independently of the other hydrogen, $C_1$–$C_6$alkyl, $C_1$–$C_6$alkoxy, $C_1$–$C_6$haloalkyl, $C_5$- or $C_6$-cycloalkyl, unsubstituted or $C_1$–$C_4$alkyl-, $C_1$–$C_4$alkoxy-, $C_1$–$C_4$haloalkyl- or halo-substituted phenyl, or unsubstituted or $C_1$–$C_4$alkyl-, $C_1$–$C_4$alkoxy-, $C_1$–$C_4$haloalkyl- or halo-substituted benzyl. $R_{18}$ and $R_{19}$ may be, for example, methyl, ethyl, n- or iso-propyl, n-, iso- or tert-butyl, cyclohexyl, phenyl or benzyl.

Y as a diphosphine is preferably of formula IV, IVa, IVb, IVc or IVd, $$R_7R_8P-R_9-PR_{10}R_{11}, \tag{IV}$$

$$R_7R_8P-O-R_{12}-PR_{10}R_{11}, \tag{IVa}$$

$$R_7R_8P-NR_c-R_{12}-PR_{10}R_{11}, \tag{IVb}$$

$$R_7R_8P-O-R_{13}-O-PR_{10}R_{11}, \tag{IVc}$$

$$R_7R_8P-NR_c-R_{13}-NR_c-PR_{10}R_{11}, \tag{IVd}$$

wherein $R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N—, benzyl$_2$N—, morpholinyl, piperidinyl, pyrrolidinyl, $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;

$R_7$ and $R_8$ together and also $R_{10}$ and $R_{11}$ together form a $C_1$–$C_4$alkylene radical that is unsubstituted or substituted by $C_1$–$C_6$alkyl, by $C_1$–$C_6$alkoxy, by $C_1$–$C_6$haloalkyl, by $C_5$- or $C_6$-cycloalkyl, by unsubstituted or $C_1$–$C_4$alkyl-, $C_1$–$C_4$alkoxy-, $C_1$–$C_4$haloalkyl- or halo-substituted phenyl or by unsubstituted or $C_1$–$C_4$alkyl-, $C_1$–$C_4$alkoxy-, $C_1$–$C_4$haloalkyl- or halo-substituted benzyl.

$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenyl-ene, -bicycloalkylene or -bicycloalkenylene having from 4 to 10 carbon atoms, each of which is unsubstituted or substituted by $C_1$–$C_6$alkyl, phenyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 1,4-butylene substituted in the 2,3-positions by

and unsubstituted or substituted in the 1,4positions by $C_1$–$C_6$alkyl, phenyl or by benzyl, wherein $R_{21}$ and $R_{22}$ are each independently of the other hydrogen, $C_1$–$C_6$alkyl, phenyl or benzyl; 3,4 or 2,4pyrrolidinylene or 2-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1$–$C_4$alkyl;

or Rg is a radical of the formula

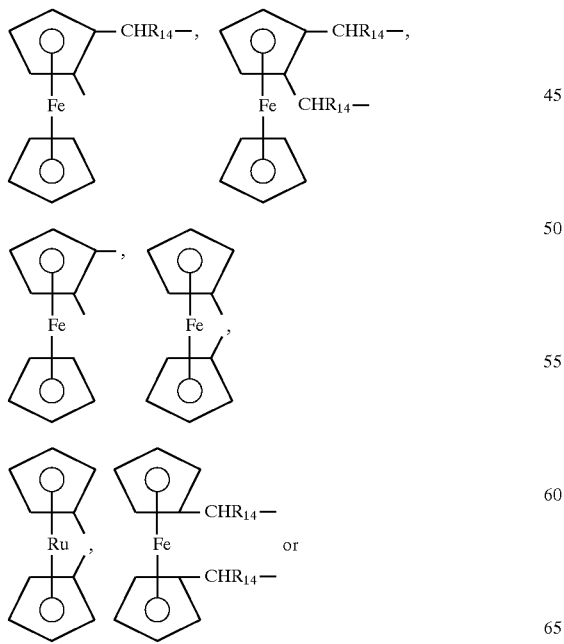

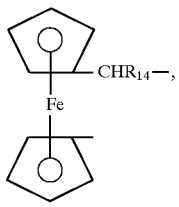

wherein $R_{14}$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents;

$R_{12}$ is linear $C_2$- or $C_3$-alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenyl-ene, -bicycloalkylene or -bicycloalkenylene having 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 3,4- or $^2$, 4-pyrrolidinylene or 3-methylene-pyrrolidin-4yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-, 2,3- or 1,8-naphthylene, each of which is unsubstituted or substituted by $C_1$–$C_4$alkyl; and $R_{13}$ is linear $C_2$alkylene that is unsubstituted or substituted by $C_1$–$C_6$alkyl, $C_5$- or $C_6$-cycloalkyl, phenyl, naphthyl or by benzyl; 1,2-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 3,4pyrrolidinylene the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene that is unsubstituted or substituted by $C_1$–$C_4$alkyl, or is a radical, less two hydroxy groups in the ortho positions, of a mono- or di-saccharide, and $R_c$ is hydrogen, $C_1$–$C_4$alkyl, phenyl or benzyl.

$R_7$, $R_8$, $R_{10}$ and $R_{11}$ are preferably identical or different, preferably identical, radicals from the following group: $C_1$–$C_6$alkyl; cyclopentyl and cyclohexyl that are unsubstituted or have from 1 to 3 $C_1$–$C_4$alkyl or $C_1$–$C_4$alkoxy substituents; benzyl and, especially, phenyl that are unsubstituted or have from 1 to 3 $C_1$–$C_4$alkyl, $C_1$–$C_4$alkoxy, F, Cl, $C_1$–$C_4$fluoro-alkyl or $C_1$–$C_4$fluoroalkoxy substituents.

A preferred subgroup of diphosphines DIP is formed by those of the formulae

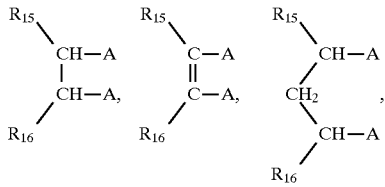

-continued

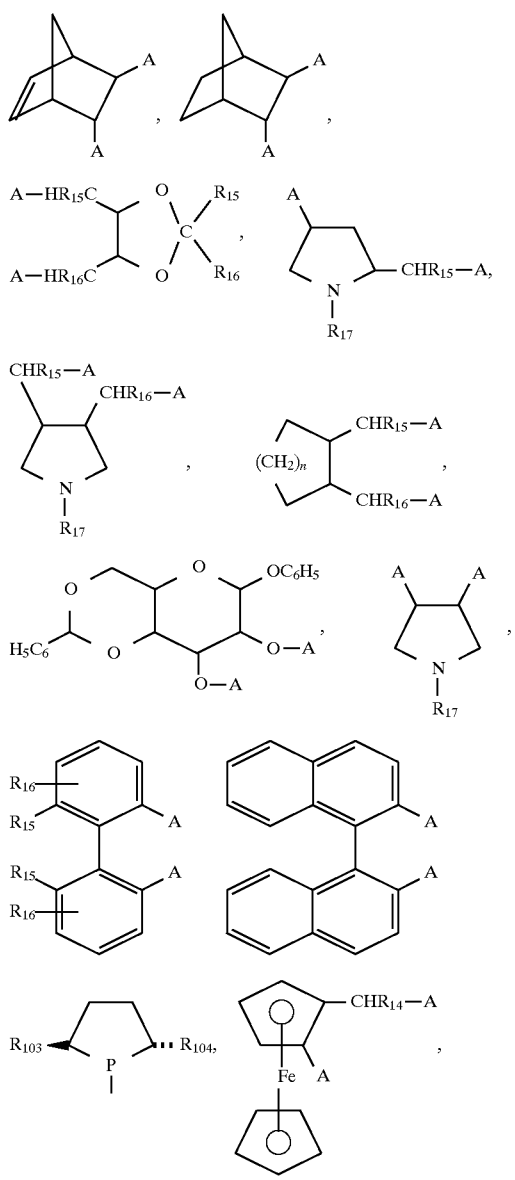

wherein
R$_{15}$ and R$_{16}$ are each independently of the other hydrogen, C$_1$–C$_4$alkyl, phenyl, benzyl, or phenyl or benzyl having from one to three C$_1$–C$_4$alkyl or C$_1$–C$_4$alkoxy substituents, R$_{14}$ is hydrogen, C$_1$–C$_4$alkyl, phenyl, benzyl, or phenyl or benzyl having from 1 to 3 C$_1$–C$_4$alkyl or C$_1$–C$_4$ailkoxy substituents, R$_{17}$ is hydrogen, C$_1$–C$_4$alkyl, phenyl, benzyl, C$_1$–C$_6$alkoxy-CO—, C$_1$–C$_6$alkyl-CO—, phenyl-CO—, naphthyl-CO— or C$_1$–C$_4$alkylNH—CO—, R$_{103}$ and R$_{104}$ are hydrogen, C$_1$–C$_4$alkyl or phenyl, A may represent identical or different groups —P(R)$_2$, wherein R is C$_1$–C$_6$alkyl, cyclohexyl, phenyl, benzyl, or phenyl or benzyl having from 1 to 3 C$_1$–C$_4$alkyl, disubstituted amino, C$_1$–C$_4$alkoxy, —CF$_3$ or partially or fully fluorinated C$_1$–C$_4$alkoxy substituents, and n is 0, 1 or 2. Of those phosphines, chirally substituted compounds are especially preferred.

Some preferred examples of diphosphines Y are (Ph is phenyl):

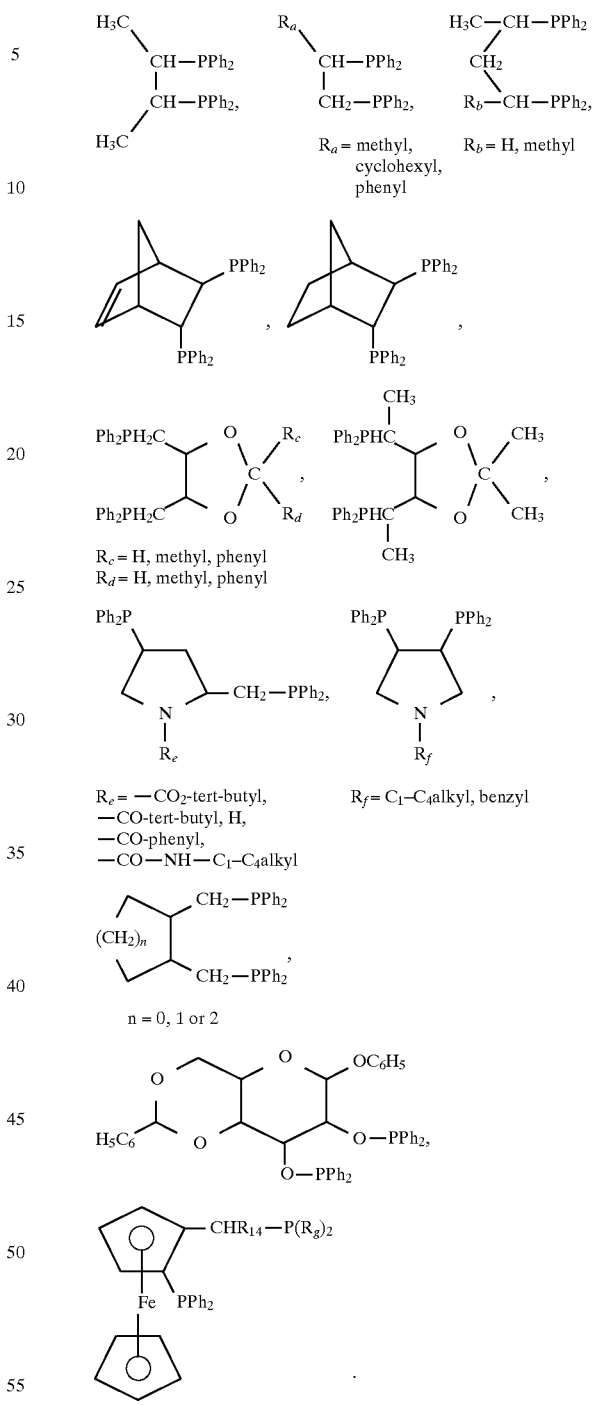

Especially suitable diphosphine ligands DIP are those wherein the secondary phosphine groups are either bonded directly or via a bridge group —CR$_a$R$_b$— in the ortho positions of a cyclopentadienyl ring or are each bonded to a cyclopentadienyl ring of a ferrocenyl, more especially those of formula X

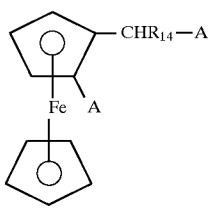

wherein $R_{14}$ is hydrogen, $C_1$–$C_4$alkyl, phenyl, benzyl, or phenyl or benzyl having from one to three $C_1$–$C_4$alkyl or $C_1$–$C_4$alkoxy substituents, and A represents identical or different groups —P(R)$_2$ wherein R is $C_1$–$C_6$alkyl, cyclohexyl, phenyl, benzyl, or phenyl or benzyl having from one to three $C_1$–$C_4$alkyl, disubstituted amino, $C_1$–$C_4$alkoxy, —CF$_3$ or partially or fully fluorinated $C_1$–$C_4$alkoxy substituents.

Preference is given to a sub-group wherein the diphosphine of formula X is chiral and $R_{14}$ is $C_1$–$C_4$alkyl, or is phenyl or benzyl having from one to three $C_1$–$C_4$alkyl or $C_1$–$C_4$alkoxy substituents, and A represents identical or different groups —P(R)$_2$ wherein R is $C_1$–$C_6$alkyl, cyclohexyl, phenyl, benzyl, or phenyl or benzyl having from one to three $C_1$–$C_4$alkyl, disubstituted amino, $C_1$–$C_4$alkoxy, —CF$_3$ or partially or fully fluorinated $C_1$–$C_4$alkoxy substituents.

Very special preference is given to the following diphosphine ligands which can be used especially in catalysts of formula (III):

{(R)-1-[(S)-2-(diphenylphosphino)ferrocenyl]}ethyl-di(3,5-dimethyl-phenyl)phosphine, {(R)-1-[(S)-2-(diphenylphosphino)ferrocenyl]}ethyl-di(3,5-dimethyl-4N,N-dipropylaminophenyl)phosphine, {(R)-1-[(S)-2-(diphenylphosphino)ferrocenyl]}ethyl-di(3,5-di-iso-propyl-4-N,N-dimethylaminophenyl) phosphine, {(R)-1-[(S)-2-(diphenylphosphino)ferrocenyl]}ethyl-di(3,5-di-iso-propyl-4-N,N-dibenzylylaminophenyl) phosphine, {(R)-1-[(S)-2-(diphenylphosphino)ferrocenyl]}ethyl-di(3,5-dimethyl-4N,N-dibenzylylaminophenyl) phosphine, {(R)-1-[(S)-2-(diphenylphosphino)ferrocenyl]}ethyl-di(3,5-dimethyl-4-(1'-pyrrolo)phenyl) phosphine, {(R)-1-[(S)-2-(diphenylphosphino)ferrocenyl]}ethyl-di(3,5-dimethyl-4-N,N-dipentylaminophenyl) phosphine, {(R)-1-[(S)-2-(diphenylphosphino)ferrocenyl]}ethyl-di(3,5-dimethyl-4-N,N-dimethylaminophenyl) phosphine, 1,4-bis(diphenylphosphino)butane, {(R)-1-[(S)-2-(di(4-methoxyphenyl)phosphino)ferrocenyl]}-ethyl-di(3,5-dimethyl-4N,N-dimethylaminophenyl) phosphine and especially {(R)-1-[(S)-2-(diphenylphosphino)ferrocenyl]}ethyl-di(3,5-dimethyl-phenyl)phosphine.

Suitable diphosphines and diphosphinites have been described, for example, by H. B. Kagan in Chiral Ligands for Asymmetric Catalysis, Asymmetric Synthesis, Volume 5, pp. 13–23, Academic Press, Inc., N.Y. (1985). The preparation of ferrocenyl diphosphine ligands is described, for example, in EP-A-0 564 406 and by T. Hayashi et al. in Bull. Chem. Soc. Jpn., 53, pages 1136–1151.

$A^\ominus$ in formula IIIa can be derived from inorganic or organic oxy acids. Examples of such acids are $H_2SO_4$, $HCl_4$, $HCl_3$, $HBrO_4$, $HIO_4$, $HNO_3$, $H_3PO_3$, $H_3PO_4$, $CF_3SO_3H$, $C_6H_5SO_3H$, $CF_3COOH$ and $CCl_3COOH$. Complex acids from which $A^\ominus$ can be derived are, for example, the halo complex acids of the elements B, P, As, Sb and Bi. Preferred examples of $A^\ominus$ in formula IIIa are $ClO_4^\ominus$, $CF_3SO_3^\ominus$, $BF_4^\ominus$, $B(phenyl)_4^\ominus$, $PF_6^\ominus$, $SbCl_6^\ominus$, $ASF_6^\ominus$ and $SbF_6^\ominus$.

When $M^\oplus$ in formula IIIb is an-alkali metal cation, it may be, for example, a Li, Na, K, Rb or Cs cation. When $M^\oplus$ is quaternary ammonium, it may contain a total of from 4 to 40, preferably from 4 to 24, carbon atoms. $M^\oplus$ may correspond to the formula phenylN$^\oplus$($C_1$–$C_6$alkyl)$_3$, benzylN$^\oplus$($C_1$–$C_6$alkyl)$_3$ or ($C_1$–$C_6$alkyl)$_4$N$^\oplus$. $M^\oplus$ in formula IIIb is preferably Li$^\oplus$, Na$^\oplus$ or K$^\oplus$ or ($C_1$–$C_6$alkyl)$_4$N$^\oplus$.

Z in formula III is preferably Br or Cl and especially Cl. Z in formula IIIb is preferably Br or I and Z in formulae IIIc and IIIEd is preferably I.

The preparation of the catalysts is known per se and is described, for example, in U.S. Pat. No. 4,994,615, U.S. Pat. No. 5,011,995, U.S. Pat. No. 5,112,999 and EP-A-0 564 406. The preparation of the catalysts of formula III can be carried out, for example, by reacting a diiridium complex of the formula [IrXZ]$_2$ with a diphosphine Y. The iridium catalysts can be added to the reaction mixture as isolated compounds. It has proved advantageous, however, to produce the catalysts in situ prior to the reaction with or without a solvent and to add optionally a portion or all of the acid and of an ammonium or metal halide.

The molar ratio of imine to iridium catalyst may be, for example, from 5 000 000 to 10, especially from 2 000 000 to 20, more preferably from 1 000 000 to 100, and more especially from 1 000 000 to 1000.

The molar ratio of imine to solid acid is, for example, from 1 000 000 to 100, preferably from 500 000 to 500, more especially from 10 000 to 1000.

The process is carried out preferably at a temperature of from −20° to 100° C., especially from 0° to 80° C. and more especially from 10° to 70° C., and preferably at a hydrogen pressure of 2×10$^5$ to 1.5×10$^7$ Pa (5 to 150 bar), especially 10$^6$ to 10$^7$ Pa (10 to 100 bar).

Within the scope of the invention, solid acids are to be understood as being those which are insoluble or only swellable in the reaction medium. Acidic inorganic or organic ion exchangers are not included, whereas ion exchangers that have been treated with acids do fall within the scope of the invention. Within the scope of the invention a solid acid is to be understood as being a solid, finely particulate and optionally porous material of which 1 g in 100 ml of water gives a pH value of ≦5, preferably ≦4 and especially ≦3.

In one embodiment the solid acids may be metal oxide systems in gel form (sol/gel systems), for example $SiO_2$, $GeO_2$, $B_2O_3$, $Al_2O_3$, $TiO_2$, $ZrO_2$ and combinations thereof. When the desired effects are not obtained to the expected extent, a considerable improvement may be achieved by treating the sol/gel systems with an acid, preferably an at least dibasic acid, such as, for example, $H_2SO_4$, $H_3PO_4$ or orthophosphoric acid. Other suitable acids are, for example, HCl, HBr, HI, $HClO_4$, $HBF_4$, HPF6, HAsF$_6$, HSbCl$_6$, HSbF$_6$ and HB(phenyl)$_4$, aliphatic and aromatic optionally halogenated (fluorinated or chlorinated) carboxylic acids, sulfonic acids and phosphorus(V) acids (for example phosphonic acids or phosphonous acids) having preferably from 1 to 20, especially from 1 to 12 and more especially from 1 to 8, carbon atoms, for example formic acid, acetic acid, propionic acid, butyric acid, benzoic acid, phenylacetic acid, cyclohexanecarboxylic acid, mono-, di- and tri-chloroacetic acid, mono-, di- and tri-fluoroacetic acid, chlorobenzoic acid, methanesulfonic acid, ethanesulfonic acid, benzenesulfonic acid, p-toluenesulfonic acid, chiorobenzenesulfonic acid, trifluoromethanesulfonic acid, methylphosphonic acid and phenylphosphonic acid. $H_2SO_4$ is preferred.

In a further embodiment, the solid acids may be inorganic or organic ion exchangers that have been treated with an at least dibasic acid, such as, for example, $H_2SO_4$, $H_2S_2O_7$ or $H_3PO_4$. Ion exchangers are known to the person skilled in the art and are described, for example, in Ullmann's Enzyklopädie der Chemischen Technik, Volume 13, 4th Edition, pages 281 to 284. Organic ion exchangers that may be mentioned are especially polymers having acidic groups, for example —C(O)OH, —SO$_3$H or —PO$_3$H (for example Nafion®), which are commercially available. Inorganic ion exchangers that may be mentioned are especially the natural and synthetic aluminosilicates, for example zeolites, which are described in Studies in Surface Science and Catalysis, Elsevier 1991, Vol. 58, chapter 2, pages 13 to 33. They are commercially available. Examples are Zeolith ZSM-5, Zeolith Y and mordenite.

In another embodiment, the solid acids may be acidic natural or synthetic silicate-like minerals that have no or only limited ion exchanging properties. Examples are phyllosilicates and argillaceous earths, for example montmorillonite, hectorite, vermicullite, kaolinite and illite. The silicates and argillaceous earths may additionally be impregnated with an acid, preferably an at least dibasic acid, such as, for example, $H_2SO_4$, $H_2S_2O_7$ and $H_3PO_4$, which enables the action to be further increased. Other suitable acids have been mentioned above.

In a further embodiment, the solid acids may be heteropoly acids which preferably consist of the elements Mo, V, W, O and H and also B, Si or P and secondary or trace elements. Such heteropoly acids are known and are described, for example, in Chemtech, page 23ff (November 1993) or Russian Chemical s Reviews, page 811ff (1987). Some examples are $H_3PW_{12}O_{40}$, $H_9PV_6Mo_6O_{40}$, $H_4SiMo_{12}O_{40}$ and $H_5BW_{12}O_{40}$.

A further suitable form of the solid acids includes non-acidic, solid, finely particulate and optionally porous carriers that have been impregnated with an acid. Suitable carriers are, for example, organic polymers, such as epoxy resins, urea/aldehyde resins, melamine/-aldehyde resins, polystyrene, ABS and polyolefins. Suitable inorganic carriers are, for example, metal and semi-metal oxides ($B_2O_3$, $Al_2O_3$, $SiO_2$, $TiO_2$, $ZrO_2$), metal nitrides, metal carbides, minerals such as silicates, and crushed stone. It will be understood that the acids must not react with the carriers. Suitable acids have been mentioned above.

The process according to the invention also comprises the additional concomitant use of a soluble ammonium chloride, bromide or iodide or a soluble metal chloride, bromide or iodide. The chlorides, bromides and iodides are used preferably in amounts of from 0.01 to 200 equivalents, especially from 0.05 to 100 equivalents and more especially from 0.5 to 50 equivalents, based on the iridium catalyst. The iodides are preferred. Ammonium is preferably tetraalkylammonium having from 1 to 6 carbon atoms in the alkyl groups, and the metal is preferably sodium, lithium or potassium. Special preference is given to tetrabutylammonium iodide, sodium iodide and potassium iodide. Provided that they are soluble in the reaction mixture and provided that oxidation reactions with other reactants can be ruled out, virtually any metal chlorides, bromides and iodides, that is to say those of the main groups and sub-groups of the Periodic Table of the Elements, can be used in the process according to the invention.

The chlorides, bromides and iodides are preferably used in concentrations of from 0.01 to 500 mmol/litre, especially from 0.01 to 50 mmol/litre, based on the volume of the reaction mixture. When hydrohalic acids, especially HI, are used in the form of solid acids, the addition of the halide is unnecessary because an ammonium salt is formed in situ with the amine formed.

The reaction can be carried out in the absence or in the presence of solvents. Examples of suitable solvents, which can be used alone or as a mixture of solvents, are: aliphatic and aromatic hydrocarbons, such as pentane, hexane, cyclohexane, methylcyclohexane, benzene, toluene and xylene; ethers, such as diethyl ether, diethylene glycol dimethyl ether, tetrahydrofuran and dioxane; halogenated hydrocarbons, such as methylene chloride, chloroform, 1,1,2,2-tetrachloroethane and chlorobenzene; esters and lactones, such as ethyl acetate, butyrolactone and valerolactone; acid amides and lactams, such as dimethylforrnamide, dimethylacetamide and N-methylpyrrolidone, and ketones, such as acetone, dibutyl ketone, methyl isobutyl ketone and methoxyacetone.

In detail, the process according to the invention can be carried out by first preparing the catalyst by dissolving, for example, (Ir-dieneCl)$_2$ and a diphosphine in a solvent or in a portion of the substance to be hydrogenated; the solid acid is then added either directly or in the form of a slurry in a solvent and imine (optionally in the form of a solution). That mixture is hydrogenated in an autoclave and the reaction mixture is isolated and purified in a manner known per se, for example by precipitation, extraction or distillation. It has proved advantageous to prepare the solid acid together with the components necessary for the catalyst formation and optionally a solvent as the initial batch and then to add the imine and to form the catalyst in situ during the initial phase of the hydrogenation.

Prior to the hydrogenation it is expedient to operate under an inert gas. It is advantageous to ensure that the catalyst solution stands for only a short time, and to carry out the hydrogenation of the imines as soon as possible after the preparation of the catalyst solution.

In the case of the hydrogenation of aldimines and ketimines, the aldimines and ketimines can also be formed in situ before or during the hydrogenation. In a preferred embodiment, an amine and an aldehyde or a ketone are mixed together and added to the catalyst solution and the aldimine or ketimine formed in situ is hydrogenated. It is also possible, however, to use an amine, a ketone or an aldehyde together with the catalyst as the initial batch and then to add the ketone or the aldehyde or the amine thereto, either all at once or in metered amounts.

The hydrogenation can be carried out continuously or batchwise in various types of reactor. Preference is given to those reactors which allow comparatively good intermixing and good removal of heat, such as, for example, loop reactors. That type of reactor has proved to be especially satisfactory when small amounts of catalyst are used.

The process according to the invention yields the corresponding amines in short reaction times while having high chemical conversion rates, with surprisingly good optical yields (ee) of 70% or more being obtained even at relatively high temperatures of more than 50° C., and even with high molar ratios of imine to catalyst.

The hydrogenated organic compounds that can be prepared in accordance with the invention, for example the amines, are biologically active substances or are intermediates for the preparation of such substances, especially in the field of the preparation of pharmaceuticals and agrochemicals. For example, o,o-dialkylarylketamine derivatives, especially those having alkyl and/or alkoxyalkyl groups, are effective as fungicides, especially as herbicides. The derivatives may be amine salts, acid amides, for example of chloroacetic acid, tertiary amines and ammonium salts (see, for example, EP-A-0 077 755 and EP-A-0 115 470).

Especially important in this connection are the optically active amines of formula VI

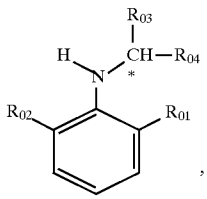
(VI)

which can be prepared from the imines of formula (V) in the presence of asymmetric iridium catalysts using the processes according to the invention and in which $R_{01}$, $R_{02}$ and $R_{03}$ are each independently of the others $C_1$–$C_4$alkyl, and Ro4 is $C_1$–$C_4$alkyl or $C_1$–$C_4$alkoxymethyl or $C_1$–$C_4$alkoxyethyl, and especially the amines of the formulae

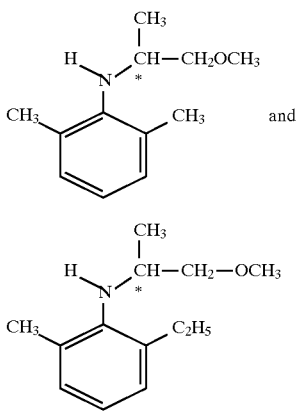

which can be prepared from the imines of formulae (Va) and (Vb) and which can be converted in accordance with methods that are customary per se with chloroacetic acid into the desired herbicides of the chloroacetanilide type; of those compounds, special preference is given to those having the S-configuration at the asymmetric C* atom.

The Examples that follow illustrate the invention in more detail. The chemical conversion is determined by gas chromatography [column: 2 m OV 100/100 to 200° C. at 10° C./min]. The optical yields (enantiomeric excess, ee) are determined either by gas chromatography [Chirasil-Val column, 50 m, manufacturer: Alltech, USA, T=150° C., isothermic], by HPLC (Chiracel OD column) or by $^1$H-NMR spectroscopy (using shift reagents).

Examples 1 to 6 and Comparison Example 20.5 g (100 mmol) of N-(2'-methyl-6'-ethyl-phen-1'-yl)-N-(1-methoxymethyl)eth-1-yl-ideneamine (purity 99.3%) are placed as the initial batch in a 50 ml microautoclave. Then 100 mg of a solid acid and a mixture of 0.15 mg (0.00045 mmol) of [Ir(1,5-cyclooctadiene)Cl]$_2$, 0.35 mg of [(R)-1-[(S)-2-(diphenylphosphino)-ferrocenyl]]ethyl-di(3,5-di-methylphenyl)phosphine and 4.5 mg (0.03 mmol) of sodium iodide are added. The autoclave is closed and, with stirring (1000 rev/min), flushed three times with argon. The stirring device is stopped and the flushing operation is repeated with hydrogen. Then the hydrogen pressure is increased to 100 bar and the autoclave is closed. The stirring device is switched on again (1400 to 1500 rev/min) and the autoclave is heated to 50° C. After 1, 2 and 3 hours, the stirring device is switched off, the autoclave is depressurised and 0.5 ml of the reaction mixture is removed using a syringe. The autoclave is then closed again and flushed three times with argon and a hydrogen pressure of 100 bar is applied. The enantioselectivity in the final sample (after 3 hours) is 76 to 77% ee (S-form). The results are summarised in Table 1 below:

TABLE 1

| Example No. | Acid | Conversion | | |
|---|---|---|---|---|
| | | 1 h | 2 h | 3 h |
| Comparison Example | none | 3 | 8 | 14 |
| 1 | ZrO$_2$ (gel) | 55 | 83 | 95 |
| 2 | SiO$_2$/ZrO$_2$ (gel) | 28 | 35 | 42 |
| 3 | H$_3$PW$_{12}$O$_{40}$ | 45 | 68 | 78 |
| 4 | SiO$_2$, impregnated with 2N H$_2$SO$_4$ | 58 | 83 | 98 |
| 5 | Zeolith Y impregnated with 2N H$_2$SO$_4$ | 59 | 89 | 99 |
| 6 | Montmorillonit KSF impregnated with 2N H$_2$SO$_4$ | 62 | 90 | 98 |

What is claimed is:

1. A process for the hydrogenation of an imine with hydrogen under elevated pressure in the presence of an iridium catalyst containing diphosphine ligands, with or without an inert solvent, the reaction mixture containing a soluble ammonium chloride, bromide or iodide or a soluble metal chloride, bromide or iodide, wherein the reaction mixture additionally contains at least one solid acid with the exception of ion exchangers.

2. A process according to claim 1, wherein the imine contains at least one >C=N—group.

3. A process according to claim 1, wherein the imine contains at least one of the groups >C=N— and >C=N—N— and additionally unsaturated groups >C=C< and >C=O.

4. A process according to claim 3, wherein the free bonds are saturated with hydrogen or organic radicals having from 1 to 22 carbon atoms or organic hetero radicals having from 1 to 20 carbon atoms and at least one hetero atom from the group O, S, N and P; or the nitrogen atom of the group >C=N— is saturated with NH$_2$ or a primary amino group having from 1 to 22 carbon atoms or a secondary amino group having from 2 to 40 carbon atoms.

5. A process according to claim 1, wherein an aldimine, ketimine or hydrazone is hydrogenated.

6. A process according to claim 5, wherein the imine is an imine of formula I

(I)

which is hydrogenated to form an amine of formula II

(II)

wherein
  $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and NR$_6$; a $C_7$–$C_{16}$aralkyl bonded via an alkyl carbon atom, or $C_1$–$C_{12}$alkyl substituted by the mentioned cycloalkyl or heterocycloalkyl or heteroaryl;
or wherein
  $R_3$ is $C_6$–$C_{12}$aryl, or $C_4$–$C_{11}$ heteroaryl bonded via a ring carbon atom and having 1 or 2 hetero atoms in the ring;

R₃ being unsubstituted or substituted by —CN, —NO₂, F, Cl, C₁-C₁₂alkyl, C₁-C₁₂alkoxy, C₁-C₁₂alkylthio, C₁-C₆haloalkyl, —OH, C₆-C₁₂-aryl or -aryloxy or -arylthio, C₇-C₁₆-aralkyl or -aralkoxy or -aralkylthio, secondary amino having from 2 to 24 carbon atoms, —CONR₄R₅ or by —COOR₄, and the aryl radicals and the aryl groups in the aralkyl, aralkoxy and aralkylthio in turn being unsubstituted or substituted by —CN, —NO₂, F, Cl, C₁-C₄-alkyl, -alkoxy or -alkylthio, —OH, —CONR₄R₅ or by —COOR₄;

R₄ and R₅ are each independently of the other hydrogen, C₁-C₁₂alkyl, phenyl or benzyl, or R₄ and R₅ together are tetra- or penta-methylene or 3-oxapentylene;

R₆ has independently the same meaning as given for R₄;

R₁ and R₂ are each independently of the other a hydrogen atom, C₁-C₁₂alkyl or cycloalkyl having from 3 to 8 ring carbon atoms, each of which is unsubstituted or substituted by —OH, C₁-C₁₂alkoxy, phenoxy, benzyloxy, secondary amino having from 2 to 24 carbon atoms, —CONR₄R₅ or by —COOR₄; C₆-C₁₂aryl or C₇-C₁₆aralkyl that is unsubstituted or substituted as R₃, or —CONR₄R₅ or —COOR₄, wherein R₄ and R₅ are as defined hereinbefore; or R₃ is as defined hereinbefore and R₁ and R₂ together are alkylene having from 2 to 5 carbon atoms that is optionally interrupted by 1 or 2 —O—, —S— or —NR₆— radicals, and/or unsubstituted or substituted by =O or as R₁ and R₂ above in the meaning of alkyl, and/or condensed with benzene, pyridine, pyrimidine, furan, thiophene or pyrrole; or R₂ is as defined hereinbefore and R₁ and R₃ together are alkylene having from 2 to 5 carbon atoms that is optionally interrupted by 1 or 2 —O—, —S— or —NR₆— radicals, and/or unsubstituted or substituted by =O or as R₁ and R₂ above in the meaning of alkyl, and/or condensed with benzene, pyridine, pyrimidine, furan, thiophene or pyrrole.

7. A process according to claim 5, wherein R₁ and R₂ as heteroaryl are a 5- or 6-membered ring having 1 or 2 identical or different hetero atoms.

8. A process according to claim 5, wherein R₁ and R₂ as heteroaryl-substituted alkyl are derived from a 5- or 6-membered ring having 1 or 2 identical or different hetero atoms.

9. A process according to claim 5, wherein R₁ and R₂ as heterocycloalkyl or as heterocycloalkyl-substituted alkyl contain from 4 to 6 ring atoms and 1 or 2 identical or different hetero atoms from the group O, S and NR₆, wherein R₆ is hydrogen, C₁-C₁₂alkyl, phenyl or benzyl.

10. A process according to claim 5, wherein R₁, R₂ and R₃ as alkyl are unsubstituted or substituted C₁-C₆alkyl.

11. A process according to claim 5, wherein R₁, R₂ and R₃ as unsubstituted or substituted cycloalkyl contain from 3 to 6 ring carbon atoms.

12. A process according to claim 5, wherein R₁, R₂ and R₃ as aryl are unsubstituted or substituted naphthyl or phenyl, and R₁, R₂ and R₃ as aralkyl are unsubstituted or substituted phenylalkyl having from 1 to 10 carbon atoms in the alkylene.

13. A process according to claim 5, wherein R₁ and R₂ together or R₁ and R₃ together form, with the carbon atom or with the —N=C group to which they are bonded, respectively, a 5- or 6-membered ring.

14. A process according to claim 5, wherein in formula I R₃ is 2,6-di-C₁-C₄alkylphen-1-yl, R₁ is C₁-C₄alkyl, and R₂ is C₁-C₄alkyl, C₁-C₄alkoxymethyl or C₁-C₄alkoxyethyl.

15. A process according to claim 14, wherein R₃ is 2,6-dimethylphen-1-yl or 2-methyl-6-ethylphen-1-yl, R₁ is ethyl or methyl, and R₂ is methoxymethyl.

16. A process according to claim 6, wherein the imine is an imine of formula

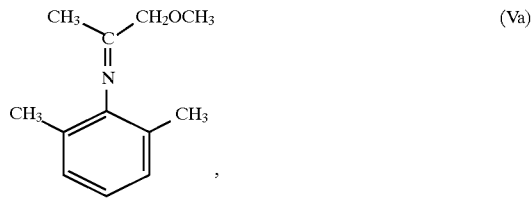

(Va)

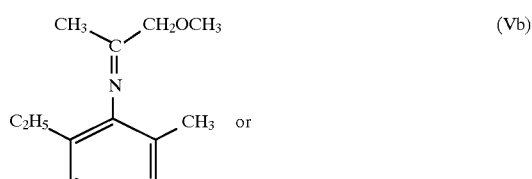

(Vb)

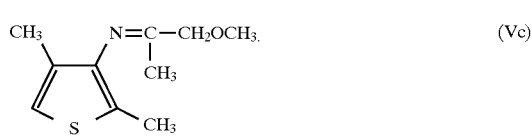

(Vc)

17. A process according to claim 1, wherein the iridium catalyst is a homogeneous catalyst that is substantially soluble in the reaction medium.

18. A process according to claim 1, wherein the catalyst corresponds to the formula III, IIIa, IIIb, IIIc or IIId

 (III)

 (IIIa)

 (IIIb)

 (IIIc)

 (IIId)

wherein X is two olefin ligands or a diene ligand, Y is a ditertiary diphosphine (a) the phosphine groups of which are bonded to different carbon atoms of a carbon chain having from 2 to 4 carbon atoms, or (b) the phosphine groups of which are either bonded directly or via a bridge group —CR$_a$R$_b$— in the ortho positions of a cyclopentadienyl ring or are each bonded to a cyclopentadienyl ring of a ferrocenyl, or (c) one phosphine group of which is bonded to a carbon chain having 2 or 3 carbon atoms and the other phosphine group of which is bonded to an oxygen atom or nitrogen atom bonded terminally to that carbon chain, or (d) the phosphine groups of which are bonded to the two oxygen atoms or nitrogen atoms bonded terminally to a C₂-carbon chain; with the result that in the cases of (a), (b), (c) and (d) a 5-, 6- or 7-membered ring is formed with the Ir atom, the radicals Z are each independently of the other(s) Cl, Br or I, A$^\ominus$ is the anion of an oxy or complex acid, and M$^\oplus$ is an alkali metal cation or quaternary ammonium, and R$_a$ and R$_b$ are each independently of the other hydrogen, C₁-C₈alkyl, C₁-C₄fluoroalkyl, phenyl or benzyl, or phenyl or benzyl having from 1 to 3 C₁-C₄alkyl or C₁-C₄alkoxy substituents.

19. A process according to claim 18, wherein the diphosphine Y contains at least one chiral group.

20. A process according to claim 18, wherein X as an olefin ligand is branched or linear $C_2$–$C_{12}$alkylene; and X as a diene ligand is an open-chain or cyclic diene having from 4 to 12 carbon atoms.

21. A process according to claim 18, wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$cycloalkyl, $C_5$–$C_{12}$cycloalkyl-$CH_2$—, phenyl or benzyl; or phenyl or benzyl substituted by halogen (e.g. F, Cl or Br), $C_1$–$C_6$haloalkyl, ($C_1$–$C_{12}$alkyl)$_3$Si, ($C_6H_5$)$_3$Si, $C_1$–$C_6$haloalkoxy (e.g. trifluoromethoxy), —$NH_2$, phenyl$_2$N—, benzyl$_2$N—, morpholinyl, piperidinyl, pyrrolidinyl, ($C_1$–$C_{12}$alkyl)$_2$N—, -ammonium-$X_1^\ominus$, —$SO_3M_1$, —$CO_2M_1$, —$PO_3M_1$ or by —COO—$C_1$–$C_6$alkyl (e.g. —$COOCH_3$), wherein $M_1$ is an alkali metal or hydrogen and $X_1^\ominus$ is the anion of a monobasic acid.

22. A process according to claim 18, wherein the diphosphine Y is of the formula:

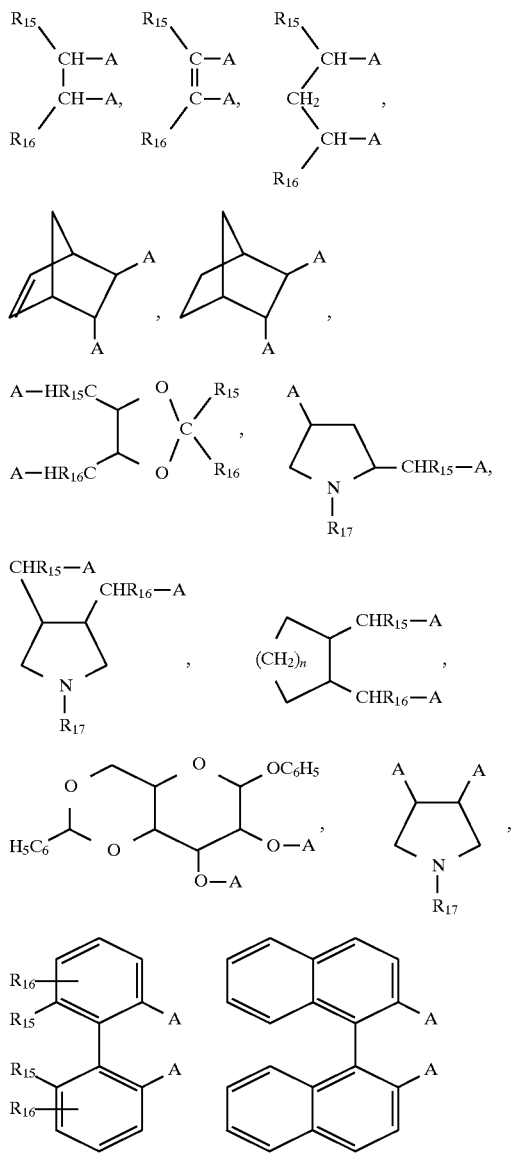

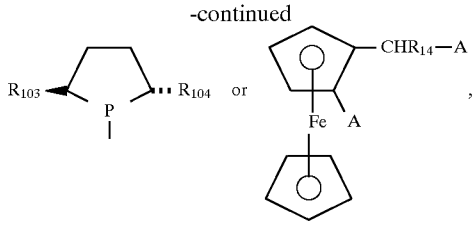

wherein $R_{15}$ and $R_{16}$ are each independently of the other hydrogen, $C_1$–$C_4$alkyl, phenyl, benzyl, or phenyl or benzyl having from one to three $C_1$–$C_4$alkyl or $C_1$–$C_4$alkoxy substituents, $R_{14}$ is hydrogen, $C_1$–$C_4$alkyl, phenyl, benzyl, or phenyl or benzyl having from 1 to 3 $C_1$–$C_4$alkyl or $C_1$–$C_4$alkoxy substituents, $R_{17}$ is hydrogen, $C_1$–$C_4$alkyl, phenyl, benzyl, $C_1$–$C_6$alkoxy-CO—, $C_1$–$C_6$alkyl-CO—, phenyl-CO—, naphthyl-CO— or $C_1$–$C_4$alkylNH-CO—, $R_{103}$ and $R_{104}$ are hydrogen, $C_1$–$C_4$alkyl or phenyl, A may represent identical or different groups —P(R)$_2$, wherein R is $C_1$–$C_6$alkyl, cyclohexyl, phenyl, benzyl, or phenyl or benzyl having from 1 to 3 $C_1$–$C_4$alkyl, disubstituted amino, $C_1$–$C_4$alkoxy, —$CF_3$ or partially or fully fluorinated $C_1$–$C_4$alkoxy substituents, and n is 0, 1 or 2.

23. A process according to claim 18, wherein the secondary phosphine groups of the diphosphine Y are either bonded directly or via a bridge group —$CR_aR_b$— in the ortho positions of a cyclopentadienyl ring or are each bonded to a cyclopentadienyl ring of a ferrocenyl.

24. A process according to claim 23, wherein the diphosphine corresponds to formula X

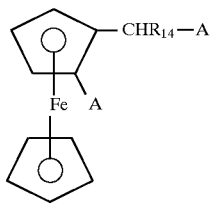

X wherein $R_{14}$ is hydrogen, $C_1$–$C_4$alkyl, phenyl, benzyl, or phenyl or benzyl having from one to three $C_1$–$C_4$alkyl or $C_1$–$C_4$alkoxy substituents, and A represents identical or different groups —P(R)$_2$ wherein R is $C_1$–$C_6$alkyl, cyclohexyl, phenyl, benzyl, or phenyl or benzyl having from one to three $C_1$–$C_4$alkyl, disubstituted amino, $C_1$–$C_4$alkoxy, —$CF_3$ or partially or fully fluorinated $C_1$–$C_4$alkoxy substituents.

25. A process according to claim 24, wherein the diphosphine of formula X is chiral and $R_{14}$ is $C_1$–$C_4$alkyl, or is phenyl or benzyl having from one to three $C_1$–$C_4$alkyl or $C_1$–$C_4$-alkoxy substituents, and A represents identical or different groups —P(R)$_2$ wherein R is $C_1$–$C_6$alkyl, cyclohexyl, phenyl, benzyl, or phenyl or benzyl having from one to three $C_1$–$C_4$alkyl, disubstituted amino, $C_1$–$C_4$alkoxy, —$CF_3$ or partially or fully fluorinated $C_1$–$C_4$alkoxy substituents.

26. A process according to claim 18, wherein the diphosphine Y is

{(R)-1-[(S)-2-(diphenylphosphino)ferrocenyl]}ethyl-di(3,5-dimethyl-phenyl)phosphine, {(R)-1-[(S)-2-(diphenylphosphino)ferrocenyl]}ethyl-di(3,5-dimethyl-4N,N-dipropylaminophenyl)phosphine, {(R)-1-[(S)-2-(diphenylphosphino)ferrocenyl]}ethyl-di(3,5-di-iso-propyl-4N,N-dimethylaminophenyl) phosphine, {(R)-1-[(S)-2-(diphenylphosphino)ferrocenyl]}ethyl-di(3,5-di-iso-propyl-4N,N-dibenzylylaminophenyl) phosphine, {(R)-1-[(S)-2-(diphenylphosphino)ferrocenyl]}ethyl-di(3,5-dimethyl-4-N,N-dibenzylylaminophenyl) phosphine, {(R)-1-[(S)-2-(diphenylphosphino)ferrocenyl]}ethyl-di(3,5-dimethyl-4-(1'-pyrrolo)phenyl)phosphine, {(R)-1-[(S)-2-(diphenylphosphino)ferrocenyl]}ethyl-di(3,5-dimethyl-4-N,N-dipentylaminophenyl) phosphine, {(R)-1-[(S)-2-(diphenylphosphino)ferrocenyl]}ethyl-di(3,5-dimethyl-4-N,N-dimethylaminophenyl) phosphine, 1,4bis(diphenylphosphino)butane or {(R)-1-[(S)-2-(di(4-methoxyphenyl)phosphino)ferrocenyl]}-ethyl-di(3,5-dimethyl-4-N,N-dimethylaminophenyl) phosphine.

27. A process according to claim 1, wherein the molar ratio of imine to iridium catalyst is from 5 000 000 to 10.

28. A process according to claim 29, wherein the molar ratio of imine to iridium catalyst is from 1 000 000 to 1000.

29. A process according to claim 1, wherein the solid acid is a solid, finely particulate and optionally porous material of which 1 g in 100 ml of water gives a pH value of ≦5.

30. A process according to claim 1, wherein the solid acid is a metal oxide system in gel form (sol/gel system).

31. A process according to claim 30, wherein the metal oxide system is $SiO_2$, $GeO_2$, $B_2O_3$, $Al_2O_3$, $TiO_2$, $ZrO_2$ or a combination thereof.

32. A process according to claim 30, wherein the sol/gel system is pretreated with an acid.

33. A process according to claim 32, wherein the acid is $H_2SO_4$, $H_3PO_4$ or orthophosphoric acid.

34. A process according to claim 32, wherein the acid is HCl, HBr, HI, $HClO_4$, $HBF_4$, $HPF_6$, $HAsF_6$, $HSbCl_6$, $HSbF_6$ or $HB(phenyl)_4$, or an aliphatic or aromatic optionally halogenated carboxylic acid, sulfonic acid or phosphorus(V) acid having from 1 to 20 carbon atoms.

35. A process according to claim 30, wherein the solid acid is an inorganic or organic ion exchanger that has been treated with an at least dibasic acid.

36. A process according to claim 30, wherein the solid acid is an acidic natural or synthetic silicate-like mineral that has no or only limited ion exchanging properties.

37. A process according to claim 36, wherein the silicate has additionally been impregnated with an acid.

38. A process according to claim 30, wherein the solid acid is a heteropoly acid.

39. A process according to claim 38, wherein the heteropoly acid comprises the elements Mo, V, W, O and H and also B, Si and P as secondary elements.

40. A process according to claim 38, wherein the heteropoly acid is $H_3PW_{12}O_{40}$, $H_9PV_6Mo_6O_{40}$, $H_4SiMo_{12}O_{40}$ or $HsBW_{12}O_{40}$.

41. A process according to claim 30, wherein the solid acid is a non-acidic, solid, finely particulate and optionally porous carrier that has been impregnated with an acid.

42. A process according to claim 41, wherein the carrier is selected from the group of organic polymers and inorganic carriers.

43. A process according to claim 41, wherein the carrier is selected from the group of metal and semi-metal oxides, metal nitrides, metal carbides, minerals, crushed stone, epoxy resins, urea/aldehyde resins, melamine/aldehyde resins, polystyrene, ABS and polyolefins.

44. A process according to claim 43, wherein the metal and semi-metal oxides are $B_2O_3$, $Al_2O_3$, $SiO_2$, $TiO_2$ and $ZrO_2$.

45. A process according to claim 1, wherein the molar ratio of imine to solid acid is from 1 000 000 to 100.

46. A process according to claim 45, wherein the molar ratio of imine to solid acid is from 10 000 to 1000.

47. A process according to claim 1, wherein the reaction temperature is from −20° to 100° C.

48. A process according to claim 1, wherein the hydrogen pressure is from 5 to 150 bar.

49. A process according to claim 1, wherein a soluble ammonium iodide or a soluble metal iodide is concomitantly used.

50. A process according to claim 1, wherein the chloride, bromide or iodide is used in an amount of from 0.01 to 200 equivalents, based on the iridium catalyst.

51. A process according to claim 1, wherein the ammonium is tetraalkylammonium having from 1 to 6 carbon atoms in the alkyl groups.

52. A process according to claim 1, wherein the metal is sodium, lithium or potassium.

53. A process according to claim 49, wherein tetrabutylammonium iodide, sodium iodide or potassium iodide is used.

54. A process according to claim 1, wherein the hydrogenation is carried out in a loop reactor.

55. A process according to claim 1, wherein an aldimine or a ketimine formed in situ before or during the hydrogenation is hydrogenated.

56. A process according to claim 1 for the preparation of a compound of formula IV

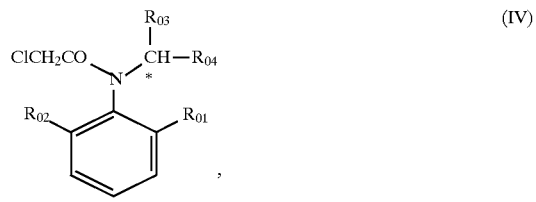

wherein $R_{01}$, $R_{02}$ and $R_{03}$ are each independently of the other $C_1$–$C_4$alkyl, and $R_{04}$ is $C_1$–$C_4$alkyl or $C_1$–$C_4$alkoxymethyl or $C_1$–$C_4$alkoxyethyl, by (1) hydrogenation of an imine of formula V

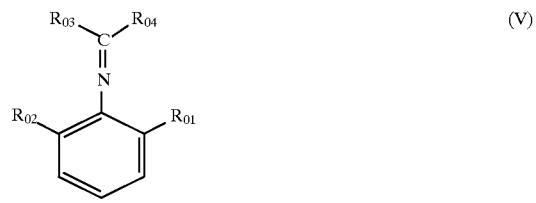

with hydrogen in the presence of an iridium catalyst and with or without an inert solvent to form an amine of formula

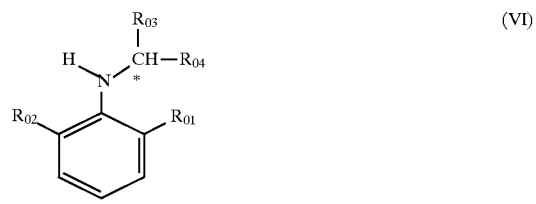

and (2) reaction thereof with the compound of formula

wherein in the hydrogenation the reaction mixture contains hydrogen iodide.

57. A process according to claim 56, wherein the imine hydrogenated is a compound of formula Va or Vb
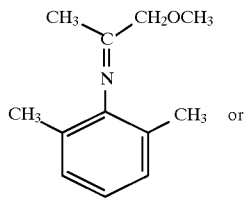
(Va)
or
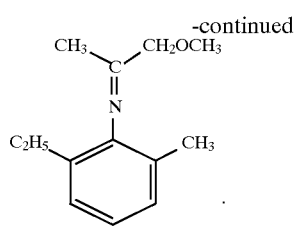
(Vb)
* * * * *